United States Patent [19]

Giner

[11] Patent Number: 4,729,824

[45] Date of Patent: Mar. 8, 1988

[54] GAS SENSOR AND METHOD OF USING SAME

[75] Inventor: Jose D. Giner, Brookline, Mass.

[73] Assignee: Giner, Inc., Waltham, Mass.

[21] Appl. No.: 918,652

[22] Filed: Oct. 14, 1986

Related U.S. Application Data

[60] Continuation of Ser. No. 697,898, Feb. 4, 1985, abandoned, which is a division of Ser. No. 430,688, Sep. 30, 1982, Pat. No. 4,508,598, which is a continuation-in-part of Ser. No. 377,143, May 11, 1982, abandoned.

[51] Int. Cl.$^4$ ............................................. G01N 27/26
[52] U.S. Cl. .................................. 204/415; 204/1 T; 204/400; 204/402; 204/406; 204/407; 204/412; 204/431; 204/433; 128/635
[58] Field of Search ............. 204/1 T, 1 K, 1 P, 1 Y, 204/400, 402, 406, 407, 412, 431, 433, 1 F, 1 N, 415; 128/635

[56] References Cited

U.S. PATENT DOCUMENTS

| | | | |
|---|---|---|---|
| 3,539,455 | 11/1970 | Clark | 204/415 |
| 4,028,207 | 6/1977 | Faktor et al. | 204/406 |
| 4,042,465 | 8/1977 | Morong et al. | 204/406 |
| 4,197,853 | 4/1980 | Parker | 204/412 |
| 4,302,315 | 11/1981 | Stetter et al. | 204/412 |
| 4,326,927 | 4/1982 | Stetter et al. | 204/406 |
| 4,340,458 | 7/1982 | Lerner et al. | 204/406 |

OTHER PUBLICATIONS

Sawyer, D. T. et al, *Experimental Electrochemistry for Chemists*, John Wiley & Sons; N.Y., N.Y., (1974) pp. 269–273.

*Primary Examiner*—Arthur P. Demers
*Attorney, Agent, or Firm*—A. W. Breiner

[57] ABSTRACT

An electrochemical sensor capable of determining the partial pressure of various gases (e.g., CO, $CO_2$, $H_2S$, alcohol vapors, hydrocarbons, $NO_x$, etc.) and, optionally, substantially concurrently, but independently, oxygen content in gases and liquids. The sensor measures the amount of chemisorbent species formed either electrochemically by partial reduction (such as "Reduced-$CO_2$" in the case of $CO_2$) or partial oxidation (in the case of alcohol) or non-electrochemically via specific adsorption (in the case of CO and hydrocarbons) on platinum or other metals. The charge required to oxidize this chemisorbed species is proportional to the amount of adsorbate on the electrode surface which is made a reproducible and reliable function of the partial pressure of the gas to be measured. By the proper selection of the sensor construction and electrical parameters, high sensitivity, fast response time, and high selectivity can be obtained.

19 Claims, 22 Drawing Figures

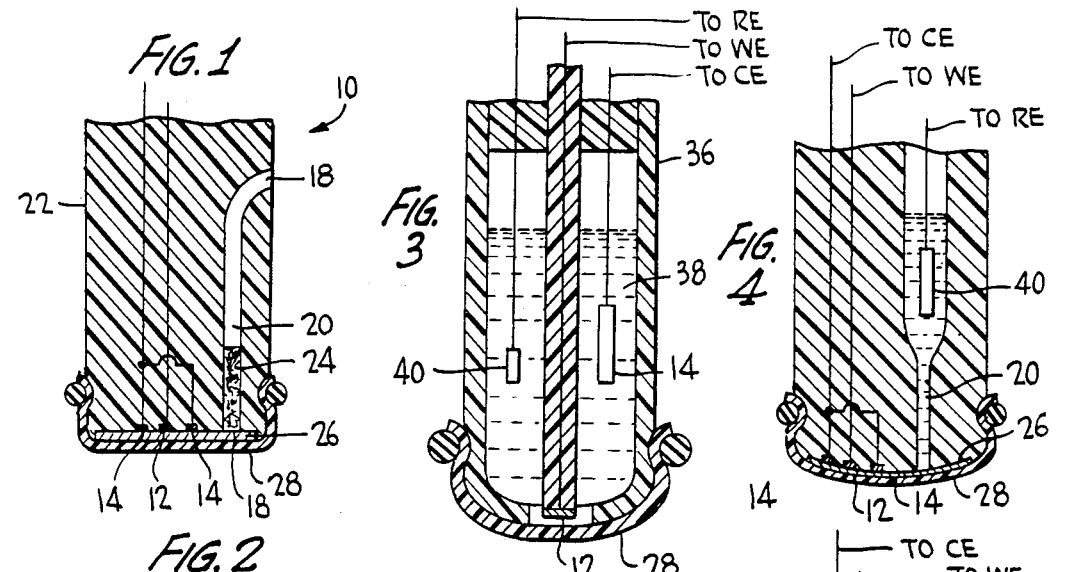
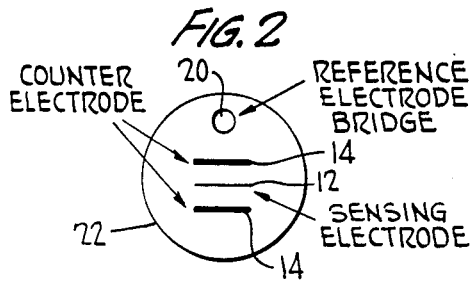
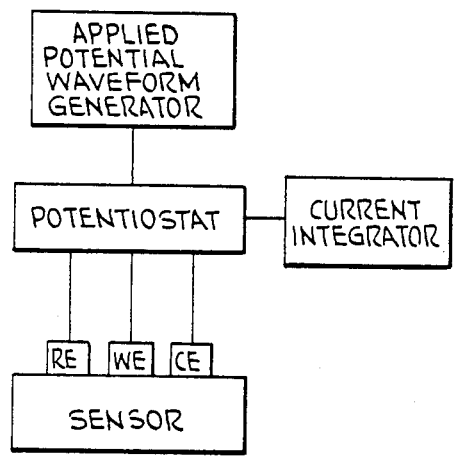
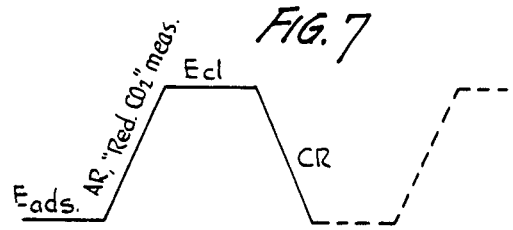
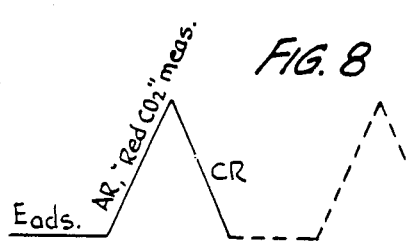

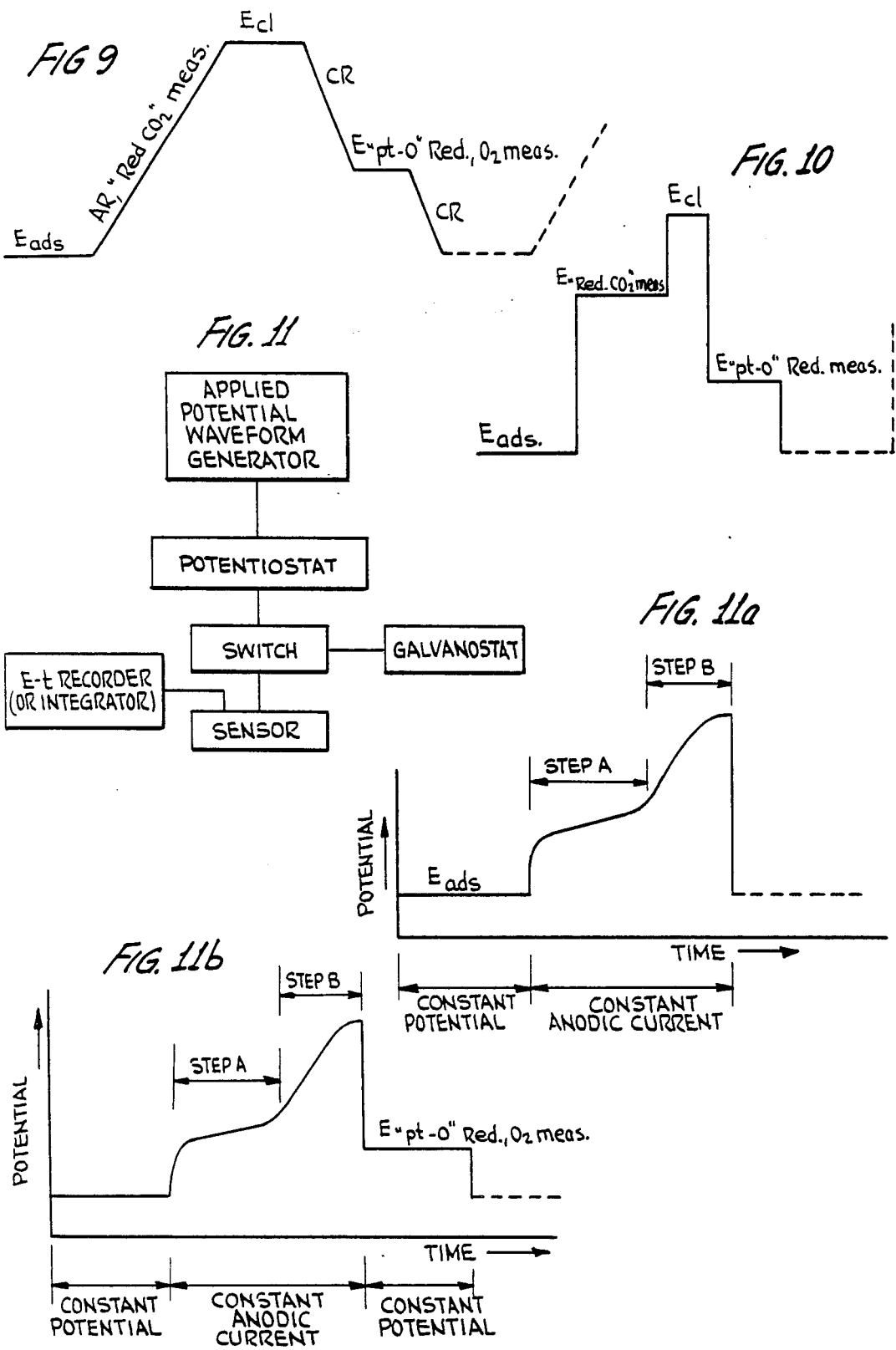

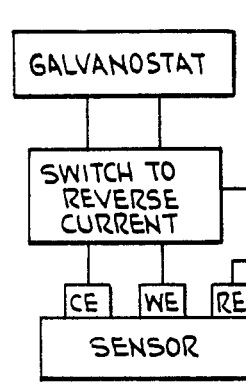
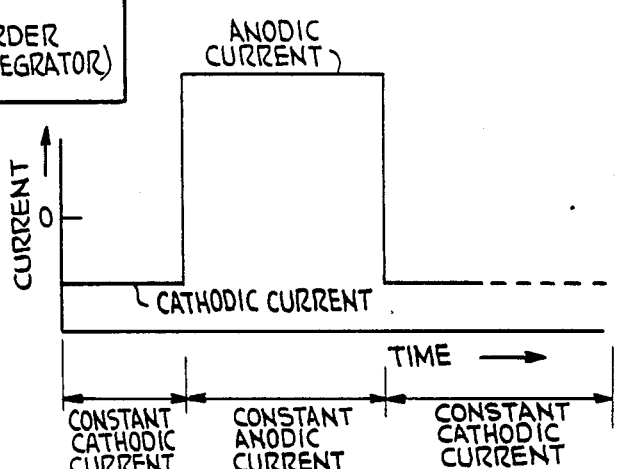
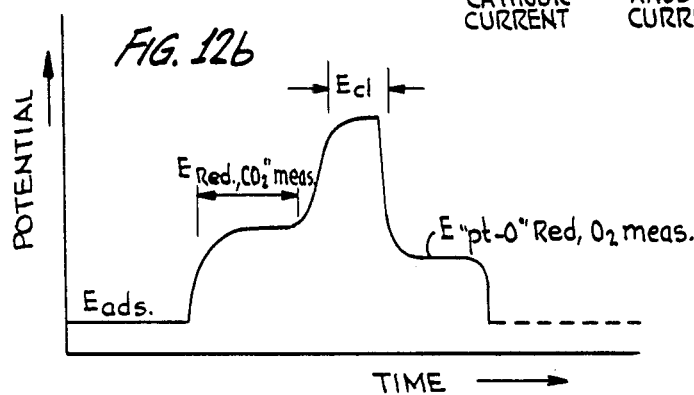
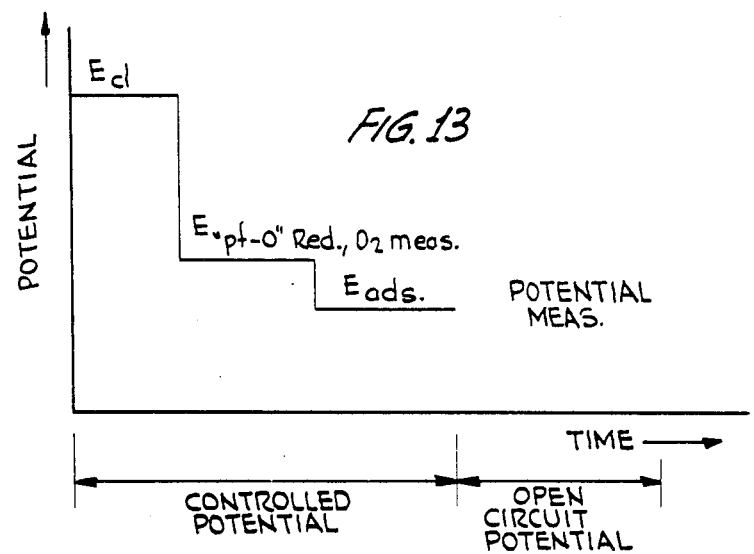

GAS SENSOR AND METHOD OF USING SAME

RELATED CASES

This is a continuation of application Ser. No. 697,898 filed Feb. 4, 1985, now abandoned, which in turn is a division of application Ser. No. 430,688 filed Sept. 30, 1982, now U.S. Pat. No. 4,508,598; which is a continuation-in-part of application Ser. No. 377,143 filed May 11, 1982, now abandoned.

FIELD OF THE INVENTION

The invention is directed to sensors for determining the concentration of various gases (including $CO_2$, CO, $H_2S$, hydrocarbons, alcohol vapors, $NO_x$, etc.) in gases and liquids electrochemically. More specifically, the invention is directed to a sensor for determining the partial pressure of gases by measuring the absorbed species formed either electrochemically by reductive adsorption (such as in the case of $CO_2$) or oxidative adsorption (such as in the case of alcohol) or non-electrochemically by specific adsorption (such as in the case of CO and hydrocarbons) on the surface of platinum and other metals; and, optionally, substantially concurrently, but independently, oxygen content in gases or liquids.

BACKGROUND OF THE INVENTION

Presently employed electrochemical gas sensors are either of the potentiometric or the polarographic type (including other current measuring approaches).

Potentiometric sensors are basically modified pH-electrodes whose operating principle is based on the measurement of a potential that is effectively a linear function of the logarithm of H+ ion concentration. Typically, electrochemical sensors for carbon dioxide, hydrogen sulfide, nitrogen oxides, sulfer dioxide, etc., belong to this category. As an example, the relationship between pH and the partial pressure of carbon dioxide ($P_{CO_2}$) in the sensor is $$\Delta pH = 0.97 \, \Delta \log_{10} P_{CO_2}.$$

Since one unit of pH at room temperature corresponds to less than 60 mV potential change, it is obvious that this type of measurement is intrinsically inaccurate (a change of $P_{CO_2}$ by a factor of 2 would result in a 18 mV change). Furthermore, whether a glass electrode or other types of H+ electrodes such as a palladium/palladium oxide, iridium/iridium oxide, or a solid state ChemFET H+ electrode is used, this type of sensor has the inherent difficulties of pH-electrodes: low-sensitivity, slow response time, and considerable drift.

Polargraphic type sensors and other sensors based on a current measurement have a two-electrode or a three-electrode configuration. In either case, the working principle of this type of sensor is based on the measurement of a current, usually the limiting current, of an oxidation (or reduction) reaction involving the gas to be measured. The magnitude of this current is made proportional to the partial pressure of the gas in the environment. Typically, electrochemical sensors for oxygen, carbon monoxide, and alcohol belong to this type. The major problems of this type of sensor are low sensitivity and poor selectivity.

OBJECTS AND GENERAL DESCRIPTION OF THE PRESENT INVENTION

A primary objective of this invention is to provide an electrochemical method of measuring the partial pressure of various gases (such as CO, $CO_2$, $H_2S$, $NO_x$, alcohol vapors, hydrocarbons, etc.) by electrochemically measuring the amount of chemisorbed species formed on a metal electrode under controlled conditions.

A further objective of this invention is to provide an electrochemical method of determining the partial pressure of a number of gases, such as the ones mentioned above, and oxygen content substantially concurrently and independently with a single sensor.

A still further objective of the invention is to provide a sensor for determining the partial pressure of certain gases in gas mixtures and liquids by measuring the amount of adsorbed species formed either electrochemically (via reductive or oxidation processes) or non-electrochemically (i.e., chemisorption) on an electrode surface.

A still further objective of the invention is to provide a sensor for determining the partial pressure of various gases as mentioned above and oxygen content substantially concurrently and independently in gases and liquids with a single sensor.

These and other objects of the invention will be apparent from the following detailed description.

The realization of the objectives of this invention is based on the concept of measuring the amount of adsorbed electroactive species formed on a platinum or other electrode surface under conditions whereby this amount (coverage) is a function of partial pressure of the gas to be determined only. In the sensor configuration, the electrodes are separated from the environment by a hydrophobic membrane which is impermeable to electrolyte, but permeably to gas. Positioned behind this membrane on the electrode side is an electrolyte which is compatible with the gaseous species to be measured (in the case of $CO_2$, as an example, this electrolyte can be acid, phosphate buffer, bicarbonate solution with an inert salt, etc.). The sensor contains, in addition to the working electrode on which the adsorbed electroactive species is formed and the counter electrode, a reference electrode or an electrolytic bridge to an external reference electrode. In some situations, the counter electrode can also be used as the reference electrode. The working electrode is platinum or other precious metal such as palladium, iridium, rhodium, osmium, ruthenium, gold, and alloys thereof or alloyed with base metals, which may have a smooth or a high surface area.

Preferably the measurement is based on the potential control approach which involves the consecutive application to the working electrode, over a short period of time, of at least two potentiall pulses, using a potentiostat, as follows:

(A) The adsorbate forming potential pulse of controlled magnitude and duration at which the reaction of interest involves the formation of an adsorbed electroactive species on the working electrode either electrochemically (by partial oxidation or reduction) or non-electrochemically (by chemisorption).

The amount (coverage) of the adsorbed species is a function of the electrode potential, electrode roughness factor, gas concentration in the immediate neighborhood of the electrode, and time. The gas concentration in the immediate surrounding of the electrode is related to the partial pressure of the gas in the external environment and depends on the mass transport characteristics of the membrane and electrolyte. In a "membrane limited" sensor, the amount of adsorbate formed before saturation will depend on the membrane permeability and the partial pressure of the gas to be determined if all other factors are kept constant. Alternatively, the gas partial pressure can be determined by using kinetic rates of adsorbate formation or by using the isotherm between adsorbate coverage and gas-concentration.

(B) The measuring potential pulse during which the charge due to the oxidation of the adsorbed species is measured. This charge is a function of the partial pressure of the gas to be determined.

(C) Optionally, an activating (or cleaning) potential pulse can be included during which the electrode surface is cleansed of any impurities by applying a high (anodic) potential.

These potential "pulses" do not need to be constant potential pulses. They can be well-defined potential-time functions. The change from one potential pulse to another can either by an abrupt potential step or can occur according to a gradual potential-time function. Specifically, the measuring potential pulse can be obtained potentiodynamically, i.e., by controlling the potential-time function between the working (sensing) and reference electrode, or galvanostatically, i.e., by controlling the current between the working and counter electrodes. In both methods, the charge passed during the measuring step can be determined by electronically integrating the current and converting to partial pressure units.

Because of the presence of a hydrophobic membrane, there are no effects during the measurement by non-volatile inhibitors and co-reactants external to the membrane. Oxygen interaction can be kept very low because during the adsorbateforming pulse the current for adsorbate formation is integrated, and the current due to oxygen reduction is not included.

This electrochemical gas sensing method is highly sensitive because it integrates the current required to oxidize an adsorbed species on the electrode akin to the approach of stripping voltammetry which is commonly used in the measurement of trace metal in liquids.

This electrochemical gas sensing method is also inherently far more selective in the presence of co-reactants as compared to standard polarographic or potentiometric method because it offers a variety of choices in operating parameters and output data analysis techniques. The selectivity of the gas sensor can be significantly enhanced by:

1. Selection Of Adsorption Potential

Since the adsorption rate depends on the potential, the adsorption potential pulse becomes an important parameter in terms of selectivity of the sensor. For example, CO is adsorbed on platinum in potential regions of 0.0 to 0.75 V versus RHE, whereas $CO_2$ is reductively adsorbed in 0.0 to 0.4 V regions. Therefore, it is possible to choose a higher adsorption potential (in the region of 0.40 to 0.75 V) to eliminate the interference of $CO_2$ in the gas mixture.

2. Separation Of The Current Peaks

If more than one species is chemisorbed on the electrode, the oxidation current peaks may be well separated during the constant sweep rate anodic ramp to allow the intergration of individual peaks (or the current peak of interest) in a defined potential range. As an example, the oxidation current peaks of "Reduced-$CO_2$" and CO are approximately 100 mV apart.

Furthermore, separation of oxidation current peaks may be accomplished by varying the slope of the anodic ramp since for irreversible oxidation of an adsorbed species, the peak potential is a function of the electron transfer rate. Or the anodic ramp may be "broken" into several segments having different ramp rates. Fine tuning the ramp rates and judicious choice of the portion(s) of the output current curve for microprocessor integration can result in high selectivity.

3. Selection Of Working Electrode Material

Different materials have dissimilar adsoprtion affinities for gases. Thus, it is quite likely that in a given potential region, a specific gas will adsorb on a certain material, but not on another. For example, CO is adsorbed on platinum at potentials from 0.0 to 0.75 V (vs. RHE); whereas on rhodium, adsorption occurs from −0.2 to +0.5 V. On platinized platinum, the potentials are slightly shifted from those on smooth platinum. Likewise, the oxidation current peaks of possible interferents may occur at different potentials on different surfaces which also improves selectivity.

4. Absence Of Adsorption Current Peaks

For co-reactants such as oxygen which does not adsorb on platinum, no corresponding adsorption current peak will be observed. In this case, a limiting current (polarographic) method can be used to determine its concentration using the same sensor.

5. Control Of Sensor Operating Temperature

For example, hydrocarbons (e.g., $CH_4$) are known to adsorb strongly at higher temperatures; whereas at room temperature the coverage is rather negligible. The same sensor can be made more selective to methane by operating it at a higher temperature (e.g., 60° C. or above).

THE DRAWING AND PRESENTLY PREFERRED EMBODIMENT

In the drawing,

FIG. 1 is a longitudinal cross-section of a sensor for IN-VITRO use, not showing the reference electrode;

FIG. 2 is a transverse cross-section of the sensor of FIG. 1;

FIG. 3 is a diagrammatic cross-section along the axis of a sensor having an alternative design;

FIG. 4 is a diagrammatic cross-section along the axis of still another cell of alternative design;

FIG. 5 is a diagrammatic cross-section along the axis of still another cell of alternative design;

FIG. 6 is a block diagram of an electrochemical measuring system which is potential controlled;

FIG. 7 shows the wave shape of a potential controlled sensor cycle including a cleaning step;

FIG. 8 shows the wave shape of a potential controlled sensor cycle without a cleaning step;

FIG. 9 illustrates an alternative wave shape of a potential controlled sensor cycle;

FIG. 10 is still another alternative wave shape of a potential controlled sensor cycle;

FIG. 11 is a block diagram of an electrochemical measuring system which is potential controlled/galvanostatically controlled;

FIGS. 11a and 11b illustrate potential-time curves of a potential controlled/galvanostatically controlled (current controlled) measuring system;

FIG. 12 is a block diagram of an electrochemical measuring system which is galvanostatically controlled;

FIGS. 12a and 12b illustrate current-time and potential-time curves of a galvanostatically controlled measuring system;

FIG. 13 is a potential-time curve for the reductive adsorption and measuring of carbon dioxide on an electrode surface wherein measurement is at open circuit potential;

Figure 14:
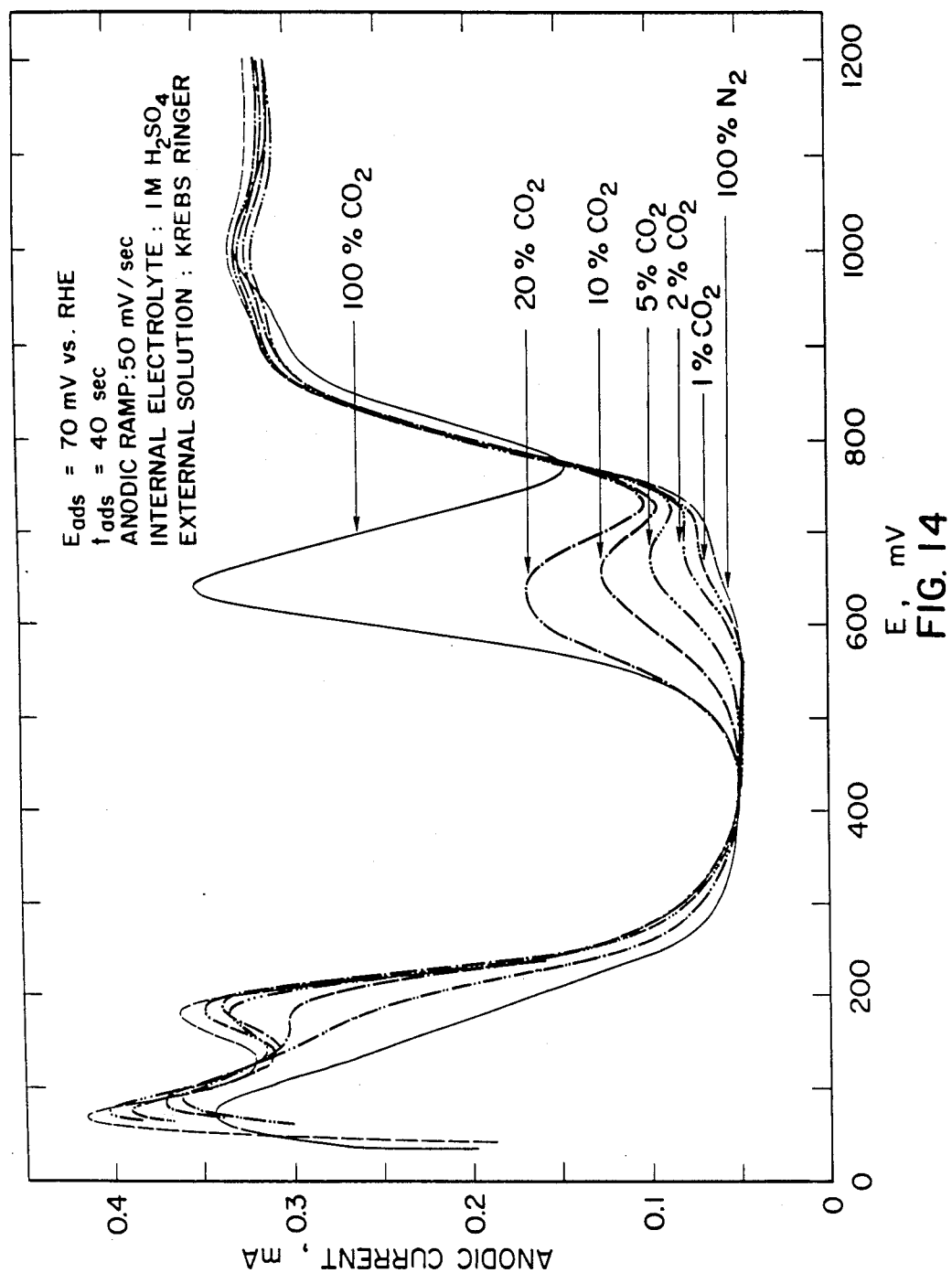
FIG. 14 shows current-potential curves for different concentrations of carbon dioxide obtained after reductive adsorption of 70 mV versus a reversible hydrogen electrode for 40 seconds.

As illustrated in FIGS. 1 and 2, a sensor 10 to measure carbon dioxide in liquids includes a plastic cylinder 22; an rectangularly shaped platinum working electrode 12, approximately 1.25 mm×6 mm, which is sandwiched between two interconnected platinum counter electrodes 14 of similar shape and size positioned in parallel relation. The surfaces of the electrodes were ground flush with 240, 320, 400, and 600 grit SiC paper. The flush surfaces were then platinized to render a surface roughness factor of approximately 100.

The smooth basal surface of the resin has an opening 18 for a capillary 20 running parallel to the cylinder axis. This capillary, filled with hyrophilic fibers 24 to avoid convection, is used as an ionic bridge for the reference electrode. A 125μ thick non-woven glass fiber spacer 26 prewetted with electrolyte (internal electrolyte) is placed over the surfaces of the electrodes and a 25μ thick Teflon membrane 28 having a 0.2μ pore size is mounted over the wetted spacer to separate the internal electrolyte from the external environment.

EXAMPLE 1—$CO_2$ MEASUREMENT

As an example, the capability of this electrochemical sensing method to measure carbon dioxide has been investigated in liquids containing dissolved carbon dioxide under the following conditions: 1M $H_2SO_4$ is employed as the internal electrolyte and a Krebs-Ringer solution is the liquid containing the carbon dioxide. [A Krebs-Ringer solution is composed of NaCl=0.109M; KCl=0.004M; $NaHCO_3$=0.024M; $MgSO_4$=0.0006M, and $NaH_2PO_4$=0.001M.] The temperature of the electrochemical cell is maintained at 37° C. A dynamic hydrogen electrode (DHE) was used as the reference electrode. The results are reported versus the reversible hydrogen electrode (RHE). Premixed and preanalyzed $CO_2/N_2$ mixtures were used which covered a wide $P_{CO_2}$ range from 0 to 760 mm mercury. The gas was first passed through a presaturator maintained at 37° C. before entereing the cell. The cell was allowed to equilibrate for at least 20 minutes before any measurements were made for a new gas composition.

Figure 15:
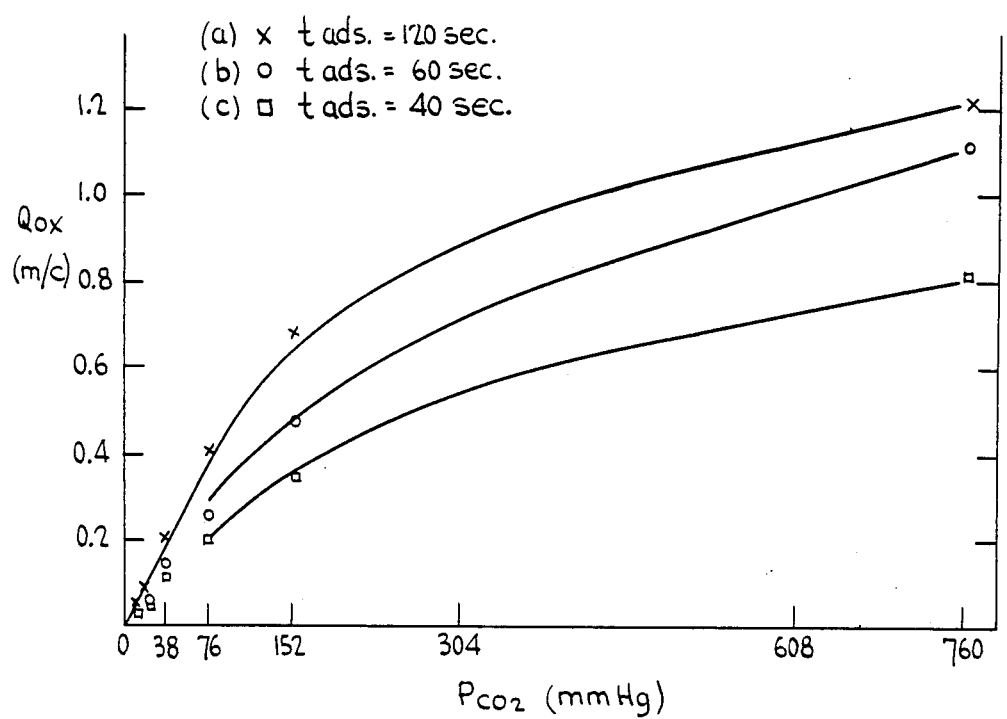
FIG. 15 is a series of $Q_{ox}$ versus $P_{CO_2}$ curves showing the effect of $t_{ads}$.

Prior to the measurements, the working electrode was cleaned by cycling it from 0 to 1500 mV (vs. RHE) using a triangular wave form similar to that shown in FIG. 8 at a sweep rate of 500 mV/sec. The potential of the working electrode was then brought to $E_{ads}$ (70 mV vs. RHE) for a period of $t_{ads}$ (which in three sets of measurements was, respectively, 40, 60, and 120 seconds) to allow reductive adsorption of carbon dioxide to take place. This was immediately followed by an applied anodic potential ramp (AR) at a sweep rate of 50 mV/sec to oxidize the adsorbed "Reduced-$CO_2$" species. The oxidation current was recorded as a function of potential shown in FIG. 14. The current peak located in the 500 to 800 mV (vs. RHE) potential region is due to the "Reduced-$CO_2$" oxidation. This current was integrated into charge ($Q_{ox}$) (with subtraction of the background charge, i.e., charge with no $CO_2$ present) which was used as a measure of chemisorbed "Reduced-$CO_2$" to quantitatively determine $P_{CO_2}$. Or, the current peak could also be used as an indication of $Q_{ox}$ and, thus, $P_{CO_2}$. A Princeton Applied Researcy 173 potentiostat, a Hewlett Packard 3310B function generator, and a Hewlett Packard 7047A X-Y recorder were used in the measurement. In FIG. 15 the integrated charge $Q_{ox}$ is shown as a function of $P_{CO_2}$ for the three sets of measurements. FIG. 15 shows that in the range from 0 to 152 mm Hg the charge varies in substantially linear manner with $P_{CO_2}$.

EXAMPLE 2—CO MEASUREMENT

As a second example, the capability of this sensor to determine carbon monoxide has been investigated in a liquid-containing dissolved carbon monoxide under the following conditions: 1M $H_2SO_4$ is employed as the internal electrolyte as well as the external fluid-containing carbon monoxide. The electrochemical measurement is carried out at room temperature. Premixed $CO/N_2$ mixtures were used which covered a wide $P_{CO}$ range from 0 to 760 mm mercury. The same precautionary procedures and experimental technique were used as the ones described in the previous example for carbon dioxide sensing.

Figure 16:
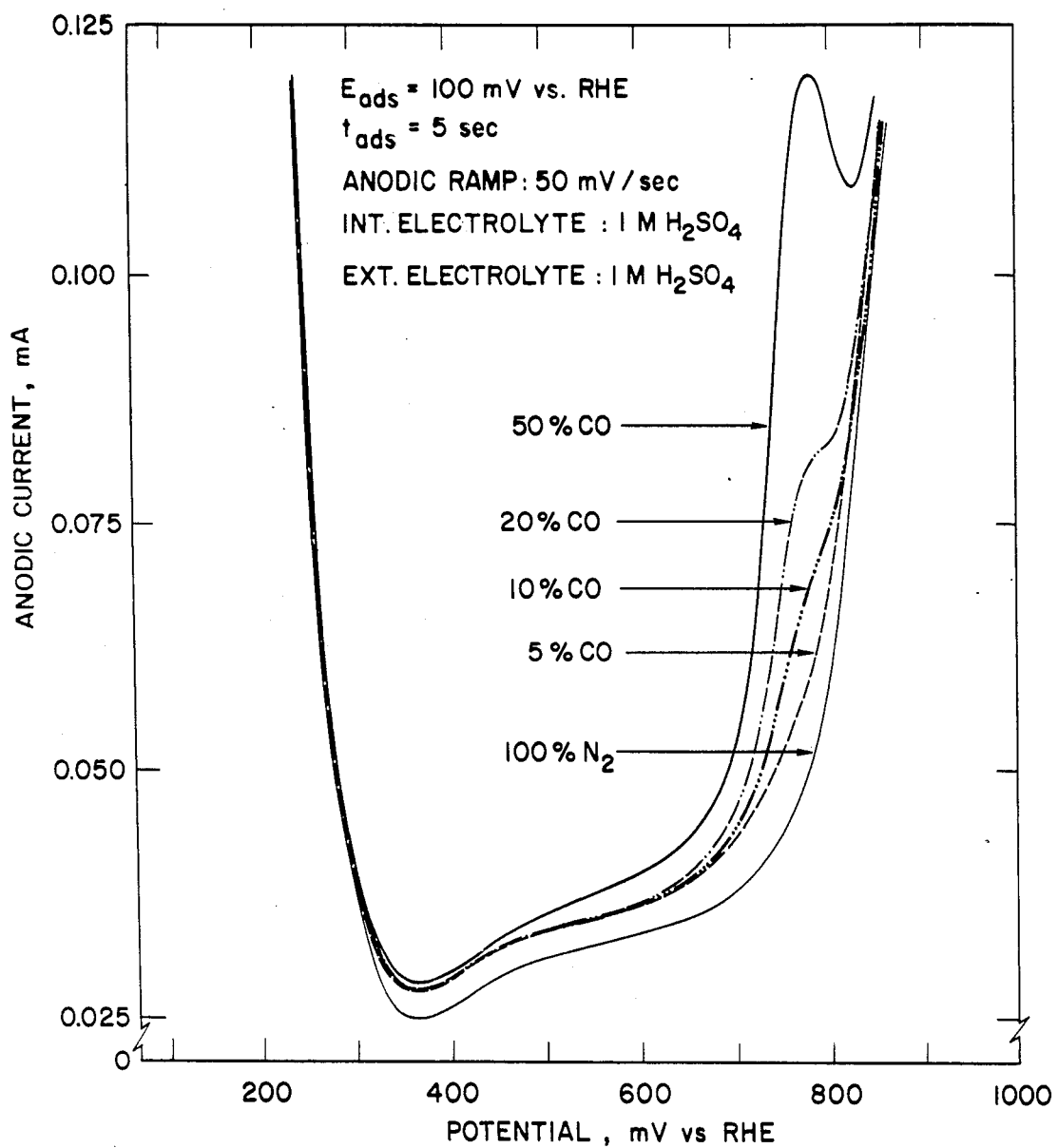
FIG. 16 shows current-potential curves for different concentrations of carbon monoxide.
Figure 17:
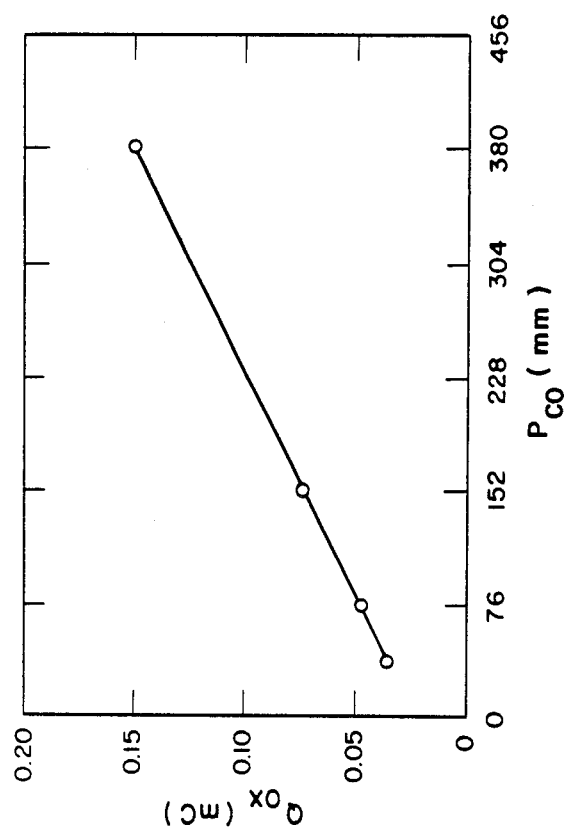
FIG. 17 is a $Q_{ox}$ versus $P_{CO}$ curve.

Prior to the measurements, the working electrode was cleaned by cycling it from 0 to 1500 mV (vs. RHE) using a triangular wave form similar to that shown in FIG. 8 at a sweep rate of 500 mV/sec. The potential of the working electrode was then brought to $E_{ads}$ (70 mV vs. RHE) for a period of $t_{ads}$ (which was 5 seconds for the actual measurements) to allow the chemisorption of CO to take place. This was immediately followed by an applied anodic potential ramp (AR) at 50 mV/sec to oxidize the chemisorbed CO on the electrode. The oxidation current was recorded as a function of potential as shown in FIG. 16. The current peak in the potential range of 700 to 900 mV is due to chemisorbed CO oxidation to $CO_2$. This current is integrated into charge ($Q_{ox}$) (substracting the background charge with no CO present) which is used as a measure of $P_{CO}$. In FIG. 17 the integrated charge $Q_{ox}$ is shown as a function of $P_{CO}$. In the range from 38 to 380 mm mercury the charge ($Q_{ox}$) varies in substantially linear relation with $P_{CO}$.

EXAMPLE 3—$H_2S$ MEASUREMENT

The detection of hydrogen sulphide has been determined in a liquid containing dissolved hydrogen sulphide under the following conditions: 1M $H_2SO_4$ is employed as the internal electrolyte as well as the external fluid containing hydrogen sulphide. The electrochemical measurement was carried out at room temperature. Premixed and preanalyzed $H_2S/N_2$ mixture at a $H_2S$ concentration of 850 ppm was used. The same precautionary measures and experimental techniques as the ones adopted in the previous examples for carbon dioxide and carbon monoxide were used.

Figure 18:
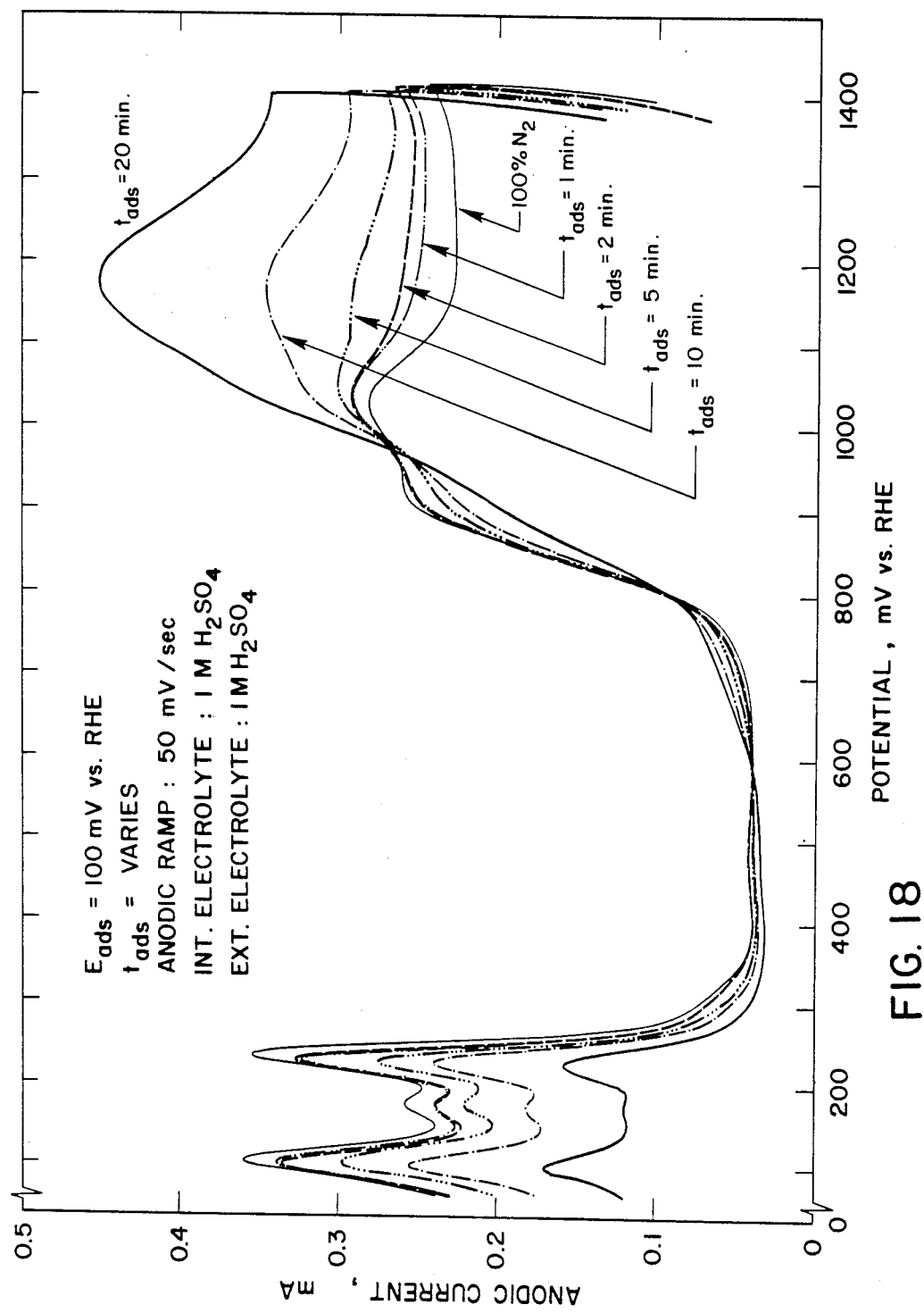
FIG. 18 shows current-potential curves for $H_2S$ at constant concentration and constant adsorption potential at varying times ($t_{ads}$).

Prior to each measurement, the platinum working electrode was cleaned by cycling from 0 to 1500 mV (vs. RHE) using a triangular wave form at a sweep rate of 500 mV/sec. The potential of the working electrode was then brought to $E_{ads}$ for a period of time $t_{ads}$ to allow the adsorption of $H_2S$ to take place. Typically, $E_{ads}$ ranged from 70 to 370 mV (vs. RHE) and $t_{ads}$ from 1 to 20 minutes. Then, it was immediately followed by an applied anodic potential ramp (AR) at 50 mV/sec to oxidize the $H_2S$ adsorbed on the electrode. The oxidation current peak was found to be 1200 mV (vs. RHE) as shown in FIG. 18. As expected, the current peak, which serves as an indicator of the amount of $H_2S$ adsorbed on the working electrode, became larger with increasing $t_{ads}$. Simultaneously, the hydrogen adsorption charge in the potential range of from 0 to 300 mV decreases as the amount of chemisorbed $H_2S$ species increases. This provides another method of measuring chemisorbed gases.

In the aforesaid gas measuring tests, the sensor can be modified as shown in FIG. 3. In FIG. 3 the sensor cell includes a housing 36, working electrode 12, and counter electrode 14. The internal electrolyte is contained in reservoir 38. Counter electrode 14 and reference electrode 40 are remotely positioned from the working electrode in the electrolyte reservoir. This sensor configuration allows gas concentration measurements in gases as well as in liquids.

As shown in FIG. 4, the reference electrode can be positioned within the cylindrical housing in accordance with the embodiment of FIG. 1, and spaced from the counter and working electrodes within an extension of capillary 20.

As shown in FIG. 5, which is a modification of the system of FIG. 1, the reference electrode can be contained within cylinder 22 and positioned substantially flush with the basal surface of the resin. In this instance the capillary 20, as such, is not essential. The working electrode, counter electrode, and reference electrode are in contact with an electrolyte impregnated within a matrix.

FIG. 6 is a block diagram of an electrochemical measuring system utilizing potential control. The reference electrode, working electrode, and counter electrode are all connected to a potentiostat which, in turn, is connected to an integrator and a wave form generator.

The sensor construction and electrical parameters of the sensor are interrelated. It is possible to predict qualitatively how changing one parameter (e.g., electrode roughness) is going to affect another parameter, e.g., time at adsorption potential, potential sweep rate for adsorbed species measurement, etc. These interrelated qualitative characteristics are used to select values for parameters when changing another parameter.

1. Sensor Construction Parameters (a) Nature Of The Electrolyte: Conditions for the electrolyte are that it (i) equilibrates with the gas to be measured; (ii) does not attach the membrane or other sensor components; (iii) has moderately high conductivity, and (iv) does not strongly adsorb on platinum, or other electrode surfaces, to the extent of interfering irreproducibly with, or excessively repressing the formation of relevant adsorbed species. As an example, for a carbon dioxide sensor acid (e.g., 0.1N $H_2SO_4$) with or without a salt, phosphate buffer, and dilute potassium bicarbonate with $Na_2SO_4$ as a supporting electrolyte can be selected.

(b) Electrode Roughness Factor: The electrode roughness factor can be varied to optimize between time response (also related to membrane characteristics), accuracy in charge measurement for a certain set of electrical parameters, oxygen effect, and magnitude of response (charge or peak current). The roughness factor can vary between about 1.5 (smooth electrode) and more than 1000. A preferred roughness factor is between about 1.5 and 200.

(c) Membrane: The hydrophobic membrane allows gas equilibrium between the external fluid (a gas or a liquid) and the electrolyte behind the membrane ("internal electrolyte"), and to ionically isolate the internal electrolyte from external fluid. If the sensor is made "membrane limited," membrane permeability is important in determining the measured current or charge. Polytetrafluoroethylene is the presently preferred membrane material. (Other suitable materials include silicones and polypropylene.) The carbon dioxide permeability of the membrane can be varied by changing the thickness, porosity, or chemical composition.

2. Electrical Parameters

A number of signal shapes can be input to the potentiostat to form the adsorbed species to quantitatively oxidize the absorbate formed, and to periodically clean the platinum surface from contamination by adventitious impurities. When the sensor is "membrane limited" as is presently preferred, a trapezoidal wave shape as illustrated in FIG. 7 can be used.

Referring to FIG. 7 for a specific wave shape, considering the single cycle (solid line), the adsorbed species is formed during the time ($t_{ads}$) at the adsorption potential ($E_{ads}$)($t_{ads}$ and $E_{ads}$ are kept fixed). The adsorbate is oxidized during the anodic potential ramp (AR); and during a fraction of this ramp, the current is integrated to determine the amount of formed adsorbate, or the current at a constant potential within the oxidation peak, or the magnitude of the peak. During the time ($t_{cl}$) at the cleaning potential ($E_{cl}$) accumulated impurities are removed from the surface of the electrode and substituted by chemisorbed oxygen which is reduced during the cathodic ramp (CR). The most important parameters in this selected wave shape are $E_{ads}$, $t_{ads}$, and the slope of the anodic ramp. Selection of $E_{ads}$ will be such that the adsorbed species is readily formed. As an example, a baseline value where $E_{ads} = +70$ mV versus the reversible hydrogen electrode in same electrolyte for measuring $CO_2$ can be used. At this potential the carbon dioxide reductive adsorption is fast and hydrogen evolution minimal. The initial selection of time of adsorption can be readily made since the saturation of the electrode with an adsorbed species is usually known (for "Reduced-$CO_2$" it corresponds to a charge of about 0.2 mCoul/cm$^2$ of electrode real surface area), and will vary with the roughness factor of the electrode studied. Another variable in the sensor is the permeability of the membrane. In a "membrane limited" sensor, the amount of adsorbate formed for a given time period before saturation will depend on the permeability of the membrane.

The slope of the ramp AR is selected so as to (i) oxidize all adsorbed species in a reasonable time; (ii) minimize activation polarization so as to avoid oxidation of the adsorbate at too high potentials, at which Pt-O formation occurs, and (iii) minimize ohmic polarization between sensing and counter electrodes. The value of the AR slope will depend on the roughness factor and typically will vary from 1 volt/sec to 10 mV/sec, which ranges from 1 second to about 1.5 minutes for a 1 volt ramp. The cleaning potential ($E_{cl}$) is between 1 volt and 1.5 volt. The duration $t_{cl}$ at $E_{cl}$ will be selected to substantially form a monolayer of chemisorbed oxygen. It is not essential to include the cleaning step since cleaning or activation at high potentials is required only after a number of cycles. In addition, if reversal from AR to CR is done at moderately high potentials (e.g., 1.5 volt), cleaning of the electrode occurs during the high potentials. The wave shape without the cleaning step is shown in FIG. 8. The value of the cathodic ramp will depend on the roughness factor and on the duration of the cleaning step.

FIG. 9 illustrates a further modified wave shape with anodic and cathodic potential ramps, with a potential step in the cathodic ramp for reducing the Pt-O film and to determine substantially concurrently the oxygen concentration of the fluid being measured.

FIG. 10 illustrates a modified wave shape with constant potential pulses which can be employed and includes also provision for reducing the Pt-O to platinum and to determine substantially concurrently the oxygen concentration of the fluid being measured.

In addition to using the potential controlled method as above described, it is possible to use variations which include galvanostatic (constant, or controlled current) pulses. (All these variations involve forming a chemisorbed species in an amount that depends only on the partial pressure of the gas to be determined.) For example, it is possible to from the adsorbed species at a constant potential step of fixed value and duration, and to follow this constant potential adsorption pulse by a galvanostatic, measuring pulse as diagrammatically illustrated in the block diagram of FIG. 11. (In practice, potentiostats can be internally wired to be switched from the potentiostatic to the galvanostatic mode.) During the galvanostatic pulse (of a fixed value), the resulting electrode potential-time curve shows a well-defined step or plateau (step A in FIG. 11a), the duration of which is proportional to the amount of adsorbed species for a fixed current. After this adsorbate oxidation step, the potential rises to oxidize the electrode surface (step B of FIG. 11a) (equivalent to a cleaning pulse). After a certain time to cover the platinum surface with chemisorbed oxygen, the operating mode is changed to the potential controlled mode, starting again the adsorption pulse. This method can be modified to substantially concurrently measure oxygen as shown in FIG. 11b. According to this method, the adsorbate is formed at a constant potential; this is followed by measuring the adsorbed species and oxidizing the platinum surface at a constant current, then the operating mode is changed to a controlled potential mode by impressing a controlled potential pulse at which the oxygen reduction current is measured after a certain duration of this pulse. The cycle is then repeated.

A number of gases (such as C, $CO_2$, $NO_x$, $H_2S$, alcohol vapors, hydrocarbons, etc.) can also be measured using a purely galvanostatic approach as shown in the block diagram in FIG. 12. According to this method, a galvanostat is connected to each of the working and counter electrodes through a switch to reverse the current flow. In turn, the working electrode and a reference electrode are connected to an E-t recorder, integrator, or timer. During the initial current flow at a fixed current and for a fixed period of time, an electroactive species is adsorbed (either electrochemically by partial reduction or oxidation, or non-electrochemically by chemisorption); and on current reversal the adsorbed species is oxidized as above. After the following cleaning step, the current is reversed again to provide a reduction of the platinum oxygen surface. During this step the oxygen can be measured by measuring the length of the step or plateau. This step is followed by the adsorbate formation step as illustrated in FIGS. 12a and 12b.

Still another method of measuring gases involves the combination of an adsorption step (potentiostatic or galvanostatic) with an open circuit potential measurement. In this method cleaning occurs at a constant potential or constant anodic current; this is followed by reveral of current or application of a potential pulse so that the platinum oxide is reduced; this is followed by the formation of the adsorbed electroactive species as the potential falls at a constant current or a step down potential pulse is applied. After the adsorbate formation at a fixed time and potential (or current), the amount of the adsorbed species is determined by measuring the open circuit potential (as illustrated in FIG. 13), which is related to this amount.

3. Simultaneous Oxygen Sensing

The sensor as above discussed can be used to determine oxygen content in a fluid by measuring the oxygen reduction current at appropriate potentials. This oxygen measurement does not interfere with the gas partial pressure measurement because the oxygen determination is a current-measurement, which can be done at potentials at which no co-reacting gases is electroactive, and the gas concentration measurement is a charge-measurement; and even if oxygen is reduced at the potentials of adsorbate formation and re-oxidation, the effect of the current due to oxygen reduction is low compared with the magnitude of the integrated current due to the formation of adsorbed species (and subsequent oxidation of the chemisorbed species). The suitability of the method to determine substantially concurrently, but independently, $P_{gas}$ and $P_{O_2}$ will depend on electrode roughness factors and on membrane permeability.

Oxygen measurement can be enhanced by modifying the wave shape. Thus, if a trapezoidal wave shape as illustrated in FIG. 8 is taken as reference, the CR can be modified by introducing a waiting time at a fixed potential (above the range of potentials of carbon dioxide reduction) at which oxygen is measured.

The sensors provided according to the present invention and the method of measuring a number of gases (e.g., CO, $CO_2$, $H_2S$, alcohol vapors, hydrocarbons, etc.) based on the determination of the coverage of an intermediate electroactive adsorbed species formed on the electrode are highly sensitive. The sensors, in addition to their being capable of miniaturization, have electrodes having little or no drift as is encountered in ion selective and solid state electrodes. Accordingly, the electrodes have unique capabilities where accuracy in determination is essential.

The internal calibration of the sensor to take into consideration background and surface area changes can be accomplished instrumentally by dividing $Q_{ox}$ by a charge or current, determined from i-E curves, which is independent of the gas concentration and dependent on electrode surface areas.

Other modifications can be made, as will be recognized by those skilled in the art, which are within the concept herein disclosed.

It is claimed:

1. A system for determining the concentration of carbon dioxide in a subject fluid comprising a sensor comprising at least a working electrode which will reductively adsorb carbon dioxide, a counter electrode, and means whereby said subject fluid containing carbon dioxide contacts said working electrode, said electrodes of said sensor being connected to a current or potential controlling device which, in turn, is connected to a current integrator, whereby carbon dioxide reductively adsorbed on said working electrode of said sensor is measured.

2. The system of claim 1 wherein said sensor is connected to a potentiostat which is, in turn, connected to a potential wave form generator and a current integrator.

3. The system of claim 2 wherein said sensor includes a reference electrode.

4. The system of claim 1 wherein said sensor is connected to a galvanostat and potentiostat through a switch, and said potentiostat is connected to an applied potential wave form generator.

5. The sensor of claim 1 wherein said sensor is connected to a galvanostat and an integrator through a switch, and said sensor includes a reference electrode which is directly connected to said integrator.

6. Apparatus for sensing and measuring a gas comprising:

(1) at least a working electrode, a counter electrode, a reference electrode, and an electrolyte inside of an enclosure and in contact with an external medium by means of a hydrophobic membrane;

(2) means to regulate the potential of the working electrode so as to produce repeatable temporal function of potential with a total period of less then five minutes, said function containing at least a potential region for formations of a gas-derived adsorbate and a potential region for measurement of the adsorbed species; and (3) means to measure amount of adsorbate.

7. A gas sensor for determining the concentration of gases in a subject fluid comprising at least a working electrode which will adsorb a gas, a counter electrode, an electrolyte in contact with each of said electrodes, a support structure, and a hydrophobic membrane; said support structure and hydrophobid membrane forming an enclosure within which said electrolyte is contained and separated from said subject fluid; said hydrophobic membrane being constructed and arranged to permit passage of gases from said subject fluid to said electrolyte for contact with said working electrode; and means for controlling the electrical potential or current of said working electrode including electrical means to form on said working electrode chemisorbed species originating from said gases, and electrical means to measure the amount of said chemisorbed species.

8. The gas sensor of claim 7 which also includes a reference electrode in contact with said electrolyte.

9. The gas sensor of claim 7 wherein the hydrophobic membrance contains a fluorocarbon polymer.

10. The gas sensor of claim 7 wherein the hydrophobic membrane contains a polymer of a silicone.

11. The gas sensor of claim 7 wherein the hydrophobic membrane contains polypropylene.

12. The gas sensor of claim 7 wherein the working electrode includes a metal of the platinum group or gold.

13. The gas sensor of claim 12 wherein the membrane is a fluorocarbon polymer.

14. The gas sensor of claim 13 wherein the electrolyte is a substantially free electrolyte.

15. The gas sensor of claim 13 wherein electrolyte is impregnated into a matrix, and said working electrode and counter electrode are in contact with said matrix.

16. The gas sensor of claim 8 wherein the reference electrode is remotely spaced from said working electrode and counter electrode, and in liquid contact with said electrolyte-impregnated matrix through an electrolyte reservoir containing electrolyte.

17. The gas sensor of claim 8 wherein electrolyte is retained in a matrix and each of said working electrode, counter electrode, and reference electrode is in contact with said matrix, and said hydrophobic membrane is in contact with the opposite surface of said matrix.

18. The gas sensor of claim 7 wherein said hydrophobic membrane is a part of said working electrode.

19. A gas sensor for determining the concentration of gases in a subject fluid comprising at least a working electrode which will adsorb a gas, a counter electrode, an electrolyte in contact with each of said electrodes; and means for controlling the electrical potential or current of said working electrode including electrical means to form on said working electrode chemisorbed species originating from said gases, and electrical means to measure said chemisorbed species.

* * * * *